(12) United States Patent
Miller, III (10) Patent No.: US 6,540,769 B1
(45) Date of Patent: Apr. 1, 2003

(54) METHOD AND APPARATUS FOR CLOSING A SEVERED STERNUM

(76) Inventor: Archibald S. Miller, III, 6585 S. Yale, Ste. 314, Tulsa, OK (US) 74136

( * ) Notice: Subject to any disclaimer, the term of this patent is extended or adjusted under 35 U.S.C. 154(b) by 0 days.

(21) Appl. No.: 10/001,988

(22) Filed: Oct. 31, 2001

(51) Int. Cl.⁷ .............................................. A61B 17/08
(52) U.S. Cl. ......................... 606/216; 24/372; 24/522
(58) Field of Search ........................ 606/71, 216, 213, 606/72, 69, 220, 215, 221, 61, 74; 292/4, 5; 128/124.1; 24/370, 372, 373, 522, 456; 269/97

(56) References Cited

U.S. PATENT DOCUMENTS

| | | | |
|---|---|---|---|
| 268,632 A | * 12/1882 | Danforth | 606/218 |
| 408,080 A | 7/1889 | Carroll | |
| 3,385,299 A | 5/1968 | Le Roy | 128/337 |
| 3,473,528 A | 10/1969 | Mishkin et al. | 128/84 |
| 3,926,193 A | * 12/1975 | Hasson | 606/218 |
| 4,201,215 A | 5/1980 | Crossett et al. | 128/335 |
| 4,279,248 A | 7/1981 | Gabbay | 128/92 |
| 4,512,346 A | 4/1985 | Lemole | 128/335 |
| 4,896,668 A | 1/1990 | Popoff et al. | 606/74 |
| 5,139,498 A | 8/1992 | Astudillo Ley | 606/69 |
| 5,318,566 A | 6/1994 | Miller | 606/60 |
| 5,330,489 A | 7/1994 | Green et al. | 606/151 |
| 5,356,412 A | 10/1994 | Golds et al. | 606/74 |
| 5,732,986 A | * 3/1998 | Piva | 292/5 |
| 5,810,825 A | 9/1998 | Huebner | 606/74 |
| 5,810,854 A | 9/1998 | Beach | 606/151 |
| 6,051,007 A | 4/2000 | Hogendijk et al. | 606/151 |
| 6,217,580 B1 | 4/2001 | Levin | 606/71 |

* cited by examiner

*Primary Examiner*—Michael J. Milano
*Assistant Examiner*—Gwen Phanijphand
(74) *Attorney, Agent, or Firm*—Head, Johnson and Kachigian (57) ABSTRACT

A sternal closure device comprising impermanently joined first and second clamp structures which are adapted for intercostal positioning between at least two corresponding rib pairs and substantially surround a patient's sternum each clamp having a cross member, a plurality of integrated legs and foot members, a plurality of sternum engagement surfaces, an end portion, a projection member, and a generally u-shaped receiving member wherein the end portions of each clamp member substantially extend toward one another when first and second clamp projection members are slidably received and secured in first and second clamp receiving chambers.

10 Claims, 7 Drawing Sheets

METHOD AND APPARATUS FOR CLOSING A SEVERED STERNUM

REFERENCE TO PENDING APPLICATIONS

This application is not related to any pending applications.

REFERENCE TO MICROFICHE APPENDIX

This application is not referenced in any microfiche appendix.

TECHNICAL FIELD OF THE INVENTION

This invention relates generally to surgical devices. More specifically, the present invention relates to improved sternum clamping devices and methods to reapproximate a patient's sternum following a partial median sternotomy.

BACKGROUND OF THE INVENTION

A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart and other thoracic organs or tissues. Following such a procedure, the two severed sternal halves must be reapproximated.

Traditionally, sternal halves have been reapproximated with stainless steel wires wrapped around or through the sternal halves so as to exert medial compression thereon and twisted together to approximate the sternum. Other methods of sternum repair include the use of band or strap assemblies which typically include a locking mechanism, which secures a strap in a closed looped configuration about the sternum positions. While utilization of steel wires and strap assemblies have been widely accepted for sternum repair, these devices present a number of disadvantages. Steel wires can and do break, and provide insufficient(non-uniform) clamping force resulting in sternal nonunion. Steel wires are difficult to maneuver and place around the sternum. The cut ends of the steel wires are also sharp and can pierce through the surgeon's gloves or fingers. In addition, the small diameter of the steel wires can cause the wires to migrate into or through the tissue surrounding the sternum region or into the sternal bone itself over time. This can lead to significant patient pain and discomfort in addition to slowing the postoperative recovery and increasing the risk of sternal infection. Moreover, the strap mechanisms of band assemblies are often relatively structurally complex and are difficult to precisely apply about the sternum. There are also healing problems associated with the use of steel wires and band assemblies due to improper forces exerted by these devices which can cause unwanted bone movements leading to raking and rubbing of surrounding tissue or bone.

Several other techniques of sternal reapproximation have been proposed both for primary closure following a median sternotomy and for reclosure following post-operative emergency surgical procedures. One such sternal fixation device is described in U.S. Pat. No. 6,051,007 entitled External Closure Device and Instruments Therefor, the entire contents of which are incorporated by reference. The sternum closure device of U.S. Pat. No. 6,051,007 however is clearly absent the benefits and teachings of the instant invention. Most particularly foot portions (20, 40) of the '007 device are limited to two points of contact on the posterior section of a patient's sternum and consequently lack the stability and positioning enhancement features of the instant invention. Quite distinguishable, from the '007 patent and other devices practiced in the contemporary art is the present invention's novel structure which allows and encourages divided sternal plates to be tilted upward to maximize healing surfaces in apposition to each other, thus avoiding downward plate deflection and substandard healing. Further, the instant invention spans the width of at least two interspaces, eliminating the need for more than one device for tight/secured closure over the same sternal area. The four securing leg and foot structures of the instant invention improve pulmonary mechanics by assisting in alignment of ribs across the sternotomy allowing for simultaneous right and left rib elevation symmetrically across the sternum and chest. The dual blade structure of the instant invention leverages the tight connections provided by fascia and muscle, strengthens pulmonary compliance and allows for distribution of energy and positioning strength to be spread evenly throughout the sternum. Most distinguishable from the contemporary art, the instant invention enables fragmented segments of the sternum to be held in place for healing, as opposed to single plate structures of the contemporary art which concentrate (as opposed to distribute) energy occassionally to a crushing central point thereby allowing laterally displaced fragments to further displace.

The above is a brief description of some deficiencies in the prior art and advantages of the present invention. Other features, advantages, and embodiments of the invention will be apparent to those skilled in the art from the following description, accompanying drawings and claims.

BRIEF SUMMARY OF THE INVENTION

The present invention provides an improved device and method for reapproximating the sternal halves of a patient's sternum following a median or partial sternotomy, and facilitates ready access to the thoracic cavity during or after a medical procedure advanced the art by overcoming the sternal nonunion problems inherent in prior art devices.

The present invention advances the present art and provides for an improved sternum clamping device which employs first and second clamp structures; and angled foot members which facilitate tilting divided sternal plates upward in apposition to each other avoiding prevent downward deflection to enhance healing.

Another significant object of the instant invention is to provide for two separate clamping devices from opposing sides which decreases the amount of metal needed for clamping/securing structures.

An additional object of the invention is to provide for two independently adjustable locking means which distribute the strength of a sternum closure, equally and laterally, and essentially appose opposing rib segments along the same plane.

Another object of the instant invention is to provide a device wherein the width of two separate intraspaces associated with the invention's clamping structures to eliminate the need for multiple devices to facilitate sternum closure over the same area.

Yet another object of the instant invention is to provide for quick release mechanism which will prevent tissue ingrowth into the clamp release mechanism.

A further object of the instant invention is to provide a small locking member and clamping apparatus which results in decreased apparatus profile and weight but not closure strength.

Yet another object of the instant invention is to provide for two member locking mechanism which improves pulmonary mechanics by assisting in the alignment of the ribs across a sternotomy, thus permitting simultaneous right and left rib elevation symmetrically across the sternum and chest.

A further object of the instant invention is to provide for a dual clamp locking mechanism which leverages ribs connected by fascia and muscle strengthening pulmonary compliance.

An additional object of the instant invention is to provide a mechanism and method by which the distribution of closure energy and strength are spread evenly throughout the sternum enabling even fragmented segments of the sternum to be held in place for healing.

Yet another object of the instant invention is to provide an apparatus by which the strength of the sternal closure is actually increased and distributed by means of a double clamping mechanism over a correspondingly positioned rib pair.

An additional further object of the instant invention is to provide an apparatus by which the alignment of apposing ribs actually increases the strength of the closure as well as pulmonary force expiratory volume.

Yet another object of the instant invention is to provide an apparatus in which the edges are smooth to prevent dehiscence or extrusion.

Other objects and further scope of the applicability of the present invention will become apparent from the detailed description to follow, taken in conjunction with the accompanying drawings wherein like parts are designated by like reference numerals.

DETAILED DESCRIPTION OF THE PREFERRED EMBODIMENT

While the making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the instant invention. While the invention has been described with a certain degree of particularity, it is clear that changes may be made in the details of construction, sequence of methodology step execution without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is intended.

Referring to the drawings like numerals indicate like elements, one embodiment of an improved sternal closure device according to the present invention is shown in FIGS. 1 through 6.

Figure 1:
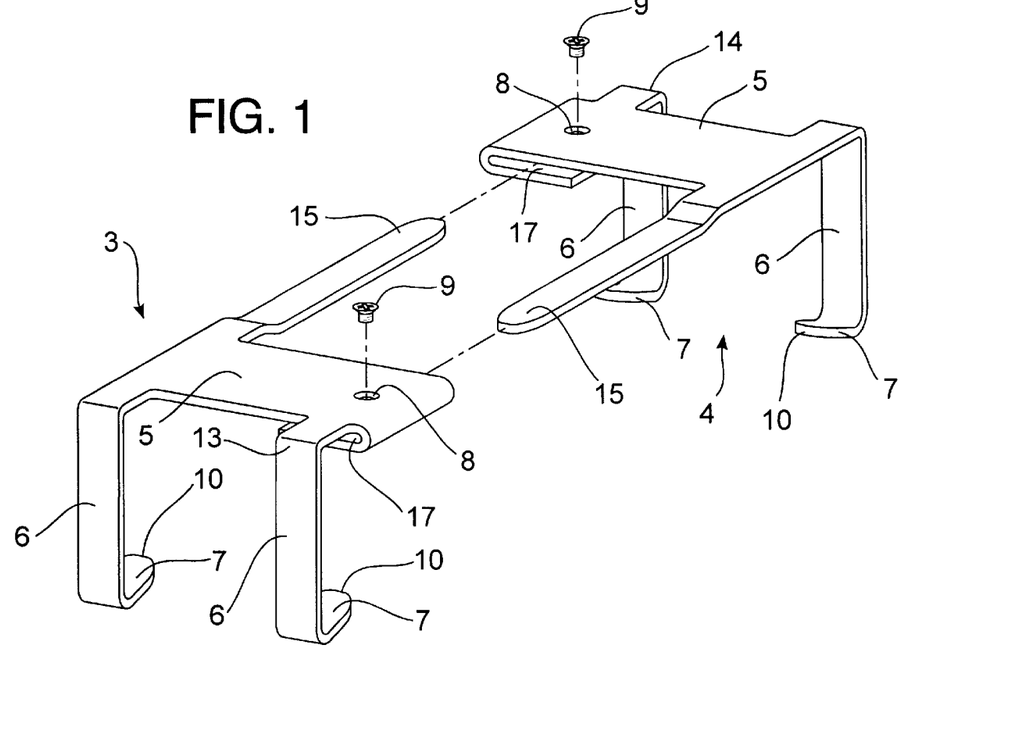
FIG. 1 illustrates clamp members of the instant invention in a disassociated or non-joined state.

FIG. 1 illustrates clamp members of the instant invention in a disassociated or non-joined state wherein first and second clamp structures (3,4) are shown. As illustrated in FIG. 1, said first and second clamp members (3,4) are identical in structure. Each of the invention's clamp members further embody a plurality of integrated leg 6 and foot members 7. It will be noted that said foot members on portions 7 are angled upwardly at approximately 20° to assist in the alignment of ribs across a severed sternum permitting simultaneous right and left rib elevation to lie symmetrically across the sternum and chest. In so doing, the elevation provided by angled foot structures 7 further assist in the alignment of apposing ribs thus increasing the position strength of invention closure as well as pulmonary forced expiratory volume.

Further illustrated in FIG. 1 are end portions 13 of each clamp generally located at the uppermost portions of said leg members 6, as are projection members 15 and general Ushaped receiving chambers 17. FIG. 1 further illustrates a plurality of sternum posterior engagement surfaces located generally on the uppermost angled portion 10 of said foot members 7. As will be discussed in association with FIG. 2a, each clamp member also embodies a frontal sternum engagement surface 19.

As can be readily envisioned, projection members 15 are slidably received into the generally Ushaped receiving chambers 17 of each clamp member (3,4). Once so positioned, said projection members 15 are secured in place via or at least one locking structure such as but not limited to a set screw 9, which is accommodated within a recessed, or bevel shaped 8 aperture located on the invention's cross member 5 said aperture 8 providing which provides access to said inserted projection member 15.

Figure 1A:
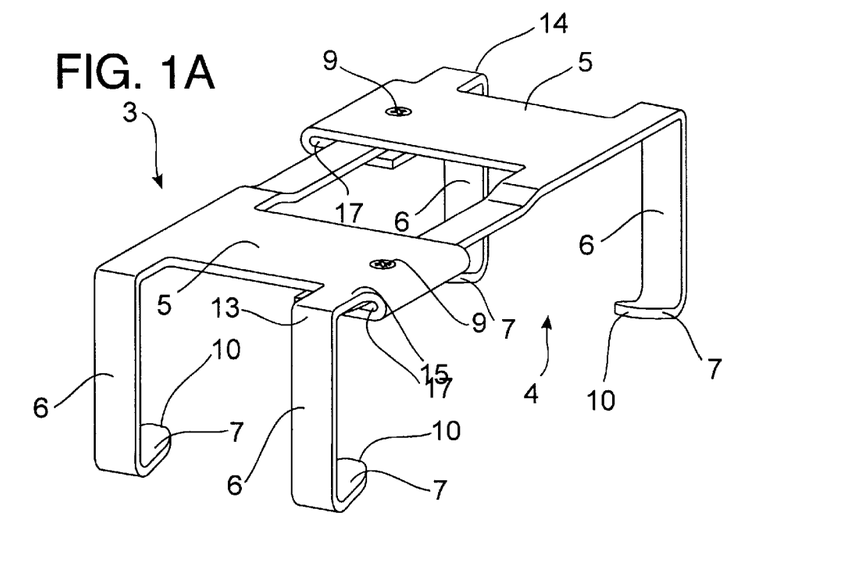
FIG. 1a illustrates the instant invention's first and second clamp members in a joined or associated state.

FIG. 1A illustrates the first and second clamp members 3, 4, illustrated in FIG. 1, in a on engaged or secured status wherein like numerals reference like invention elements. In FIG. 1a, each clamp's projection member 15, has entered a receiving chamber 17 encouraging said clamp members 3, 4 to be drawn together such that the end portion of clamp member 3, is drawn toward the end portion 14 of clamp member 4, and clamp member 4 is drawn toward the end portion 13 of clamp member 3.

Figure 2:
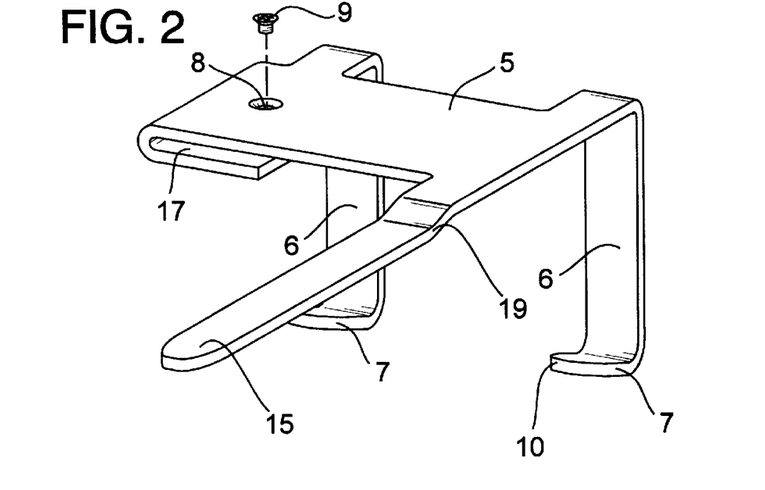
FIG. 2 is an isolated illustration of a single clamp member.

FIG. 2 illustrates a perspective view of the invention's clamp member as practiced in one embodiment wherein further detail of the invention's generally Ushaped receiving chamber 17 and recessed aperture 8 may be observed. As will be readily appreciated by those skilled in the art, said receiving chamber 17 is manifested as a Ushaped downward fold of material constituting the invention's cross member 5. Through extensive testing, it has been determined that such downward folding of said cross member 5 is most efficient to facilitate enhanced healing of a severed sternum while reducing potential for co-mingling fascia or interconnecting fibrous tissue. However, it is conceivably that the manifestation of said receiving chamber 17 could be accommodated via an upward Ushaped folding of said cross member 5 or indeed additional or secondary materials attached thereto creating a similarly intended receiving chamber.

In FIG. 2 the recess or beveled shaped aperture 8 extends through the uppermost surface of said cross member 5 to allow insertion therein of a said screw 9 or other similarly intended structure. Once a projection member 15 of an opposing clamp member is inserted in receiving chamber 17, said screw 9 or said screw equivalent structure is inserted within said beveled aperture 8 and tightened into place via a threaded or functionally equivalent means to allow the uppermost portion of said set screw structure to position itself flush with, or below, the uppermost surface crossmember 5. Once so positioned, the set screw structure 9 rests upon the inserted projection 15 member so as to fix said projection member's position within said chamber 17. Such fixation, or positioning is facilitated via influencing pressure induced by said screw structure's 9 contact with said inserted projection member 15. Further illustrated in FIG. 2 is the invention's frontal sternum engagement surface generally located in the proximity of element 19.

Figure 2A:
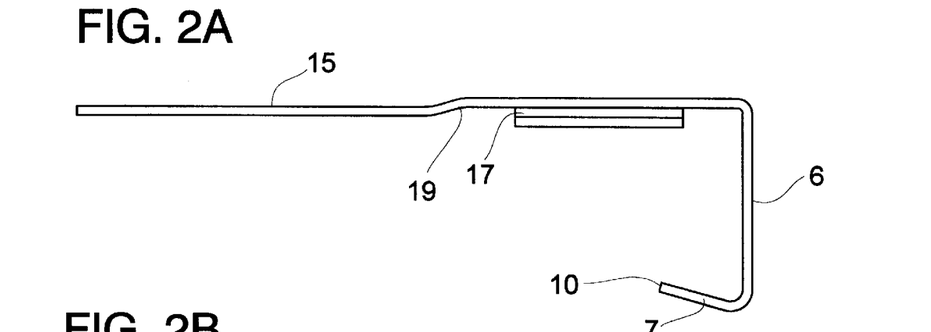
FIG. 2a is a bottom view elevation of the clamp member illustrated in FIG. 2.

FIG. 2a is a bottom elevation of the clamp member illustrated in FIG. 2 wherein like numerals indicate like elements of the embodiment of the invention disclosed in association with FIG. 1. The bottom illustration of FIG. 2a should be interpreted as viewing a horizontally positioned patient looking towards the patient's head from the patient's feet.

Figure 2B:
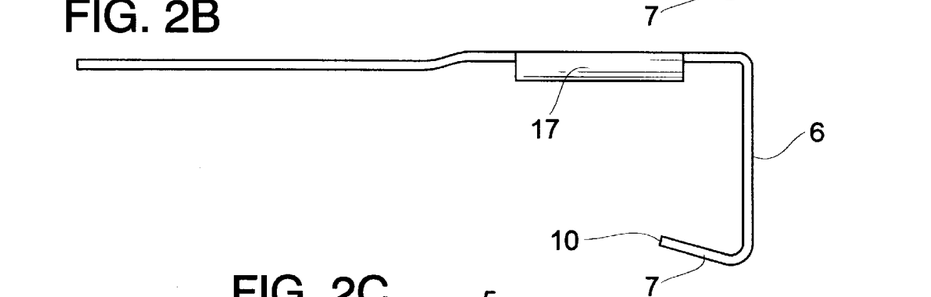
FIG. 2b is a top view elevation of the clamp member illustrated in FIG. 2.

FIG. 2b is a top elevation of the clamp member illustrated in FIG. 2 wherein like numerals indicate like elements of the embodiment of the invention disclosed in association with FIG. 1. The top illustration of FIG. 2b should be interpreted as viewing a horizontally positioned patient looking towards the patient's feet and as viewed downwardly towards the patient's head.

Figure 2C:
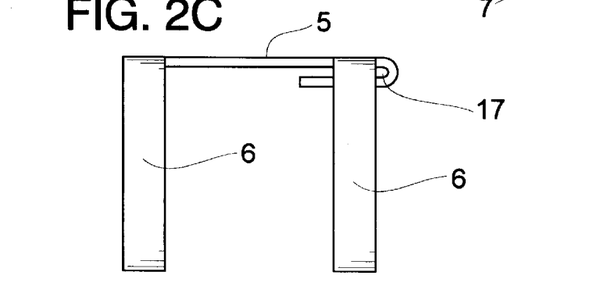
FIG. 2c is an inward view side elevation of the clamp member illustrated in FIG. 2.

FIG. 2c is an outward side elevation view of the clamp member illustrated in FIG. 2 wherein like numerals indicate like elements of the embodiment of the invention disclosed in association with FIG. 1.

Figure 2D:
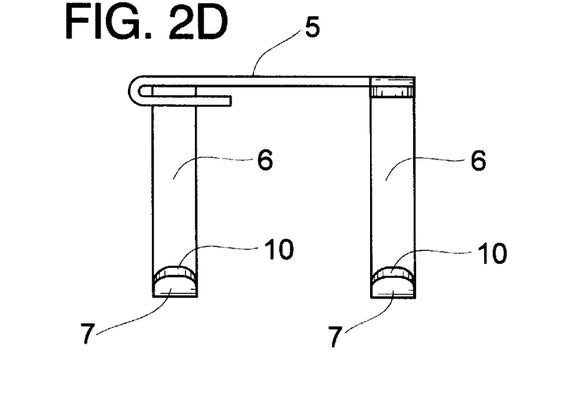
FIG. 2d is an outward view side elevation of the clamp member illustrated in FIG. 2.

FIG. 2d is an inward side elevation view of the clamp member illustrated in FIG. 2 wherein like numerals indicate like elements of the embodiment of the invention disclosed in association with FIG. 1.

Figure 2E:
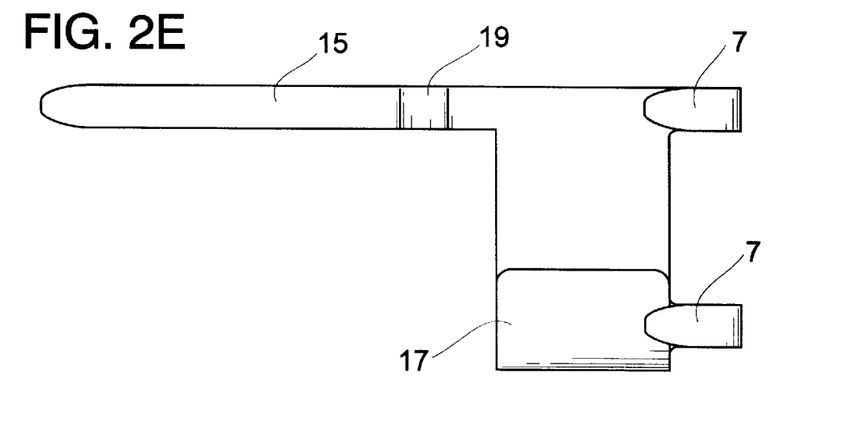
FIG. 2e is a posterior view elevation of the clamp member illustrated in FIG. 2.

FIG. 2e is a posterior view elevation of the clamp member illustrated in FIG. 2 wherein like numerals indicate like elements of the embodiment of the invention disclosed in association with FIG. 1.

Figure 2F:
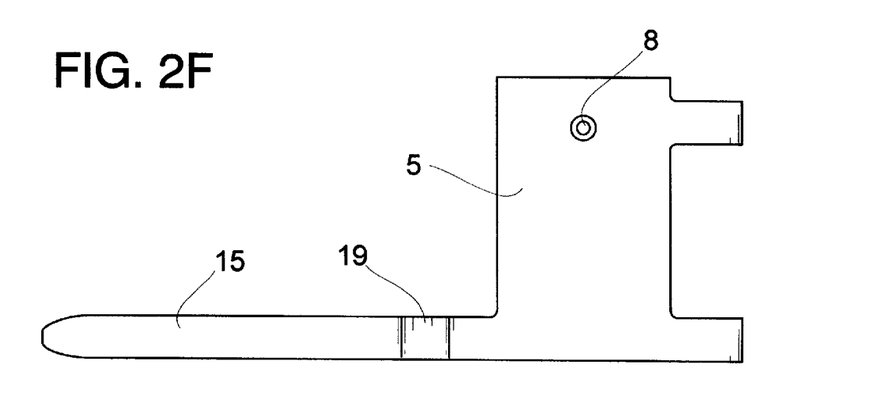
FIG. 2f is a frontal view elevation of the clamp member illustrated in FIG. 2.

FIG. 2f is a frontal elevation view of the clamp member illustrated in FIG. 2 wherein like numerals indicate like elements of the embodiment of the invention disclosed in association with FIG. 1.

Figure 3:
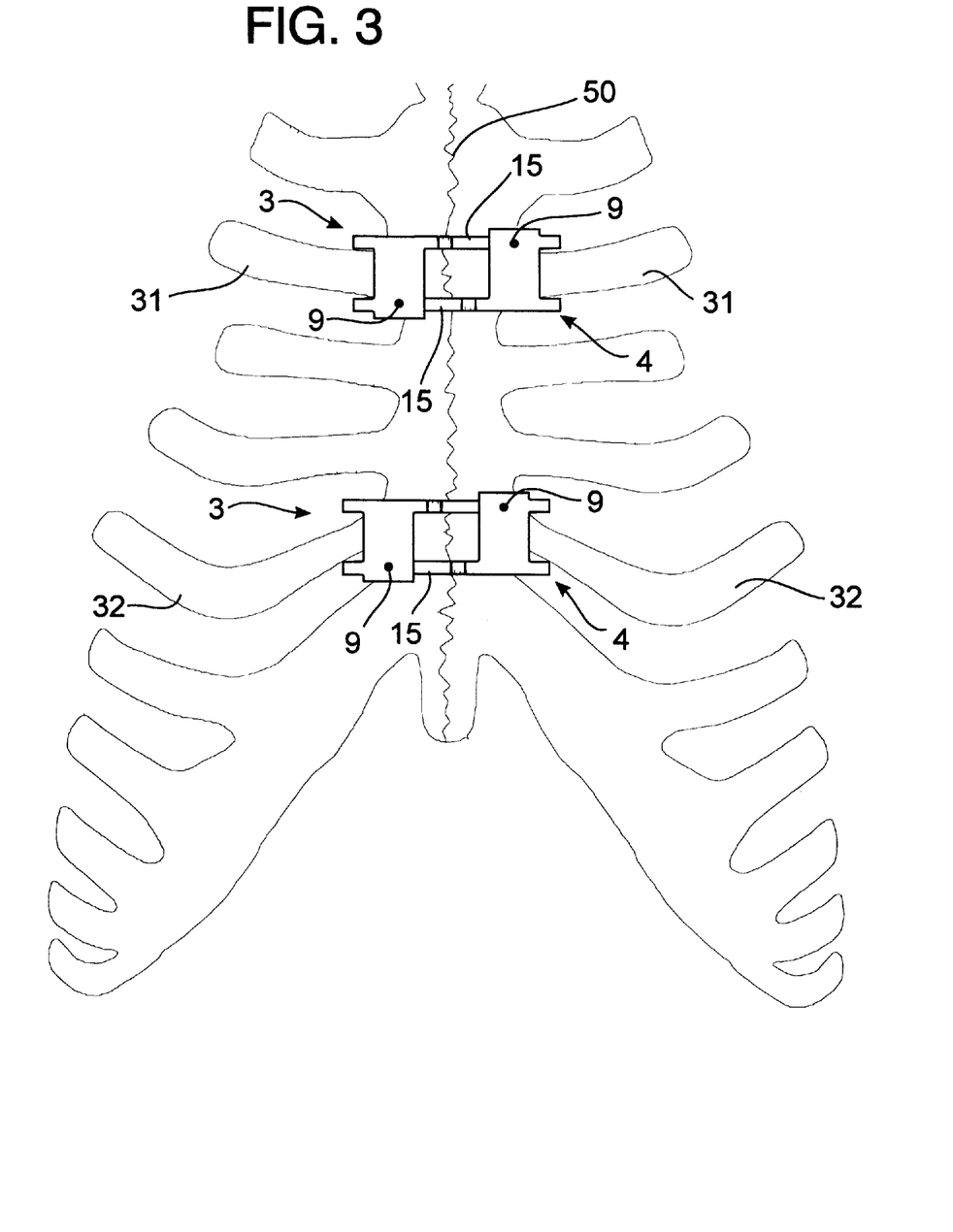
FIG. 3 illustrates a frontal view of multiple sternal closure devices intercostally positioned above and below at least two correspondingly positioned rib pairs and substantially surrounding a patient's sternum.

FIG. 3 illustrates intercostal positioning of multiple first and second clamp members 3, 4 positioned across a severed sternum 50 and between at least two correspondingly positioned rib pairs (31,32). In FIG. 3, said first and second clamp members 3, 4 have been secured together across a severed sternum 50 via insertion of each clamp's projection member 15 into an apposing clamp member's receiving chamber and having once been 50 inserted, secured in place via tightening of a set screw structure 9 which has been inserted through an aperture the uppermost portion of each clamp's cross member 5.

Figure 4:
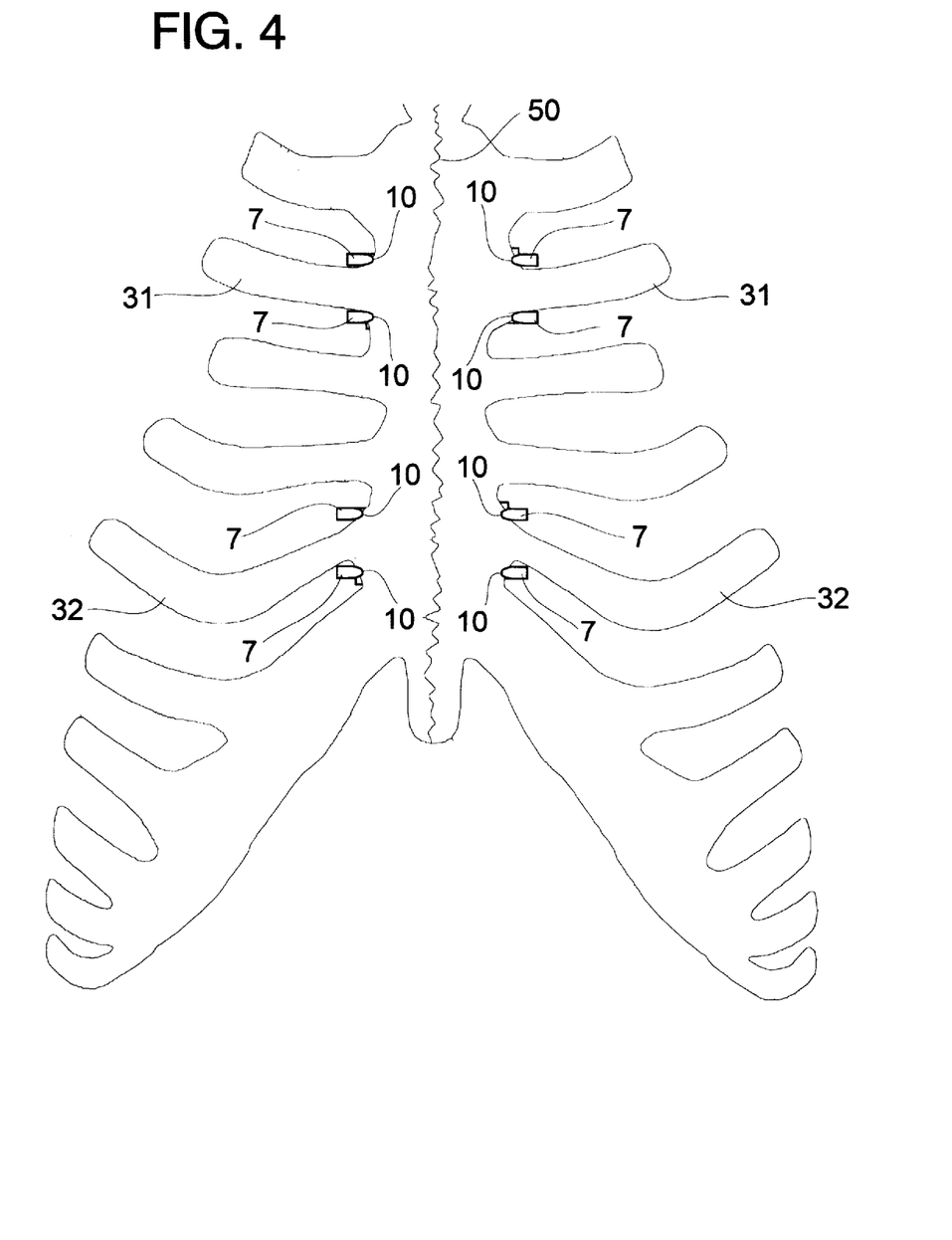
FIG. 4 illustrates a posterior view of multiple sternal closure devices intercostally positioned above and below at least two correspondingly positioned rib pairs and substantially surrounding a patient's sternum.

FIG. 4 illustrates a posterior view of multiple sternal closure devices intercostally positioned above and below at least two correspondingly positioned rib pairs (31, 32) and substantially surrounding a patient's sternum. In FIG. 4, the angled foot portions of the instant invention 7 are illustrated positioned against the posterior surface of a severed sternum 50 via each foot member's posterior engagement surface designated as element 10.

Figure 5:
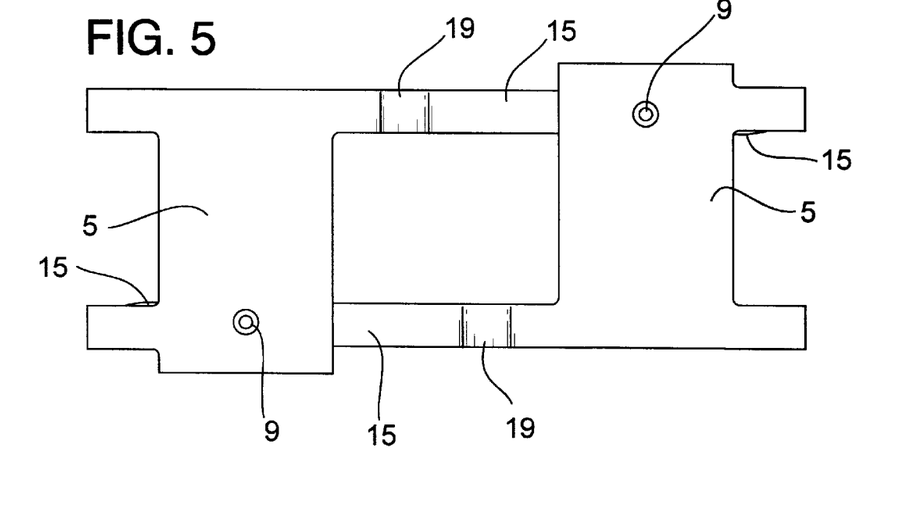
FIG. 5 illustrates a joined frontal view perspective of the invention's first and second clamp members.

FIG. 5 illustrates the frontal view perspective of the invention's closing device wherein like numerals reference like elements.

Figure 6:
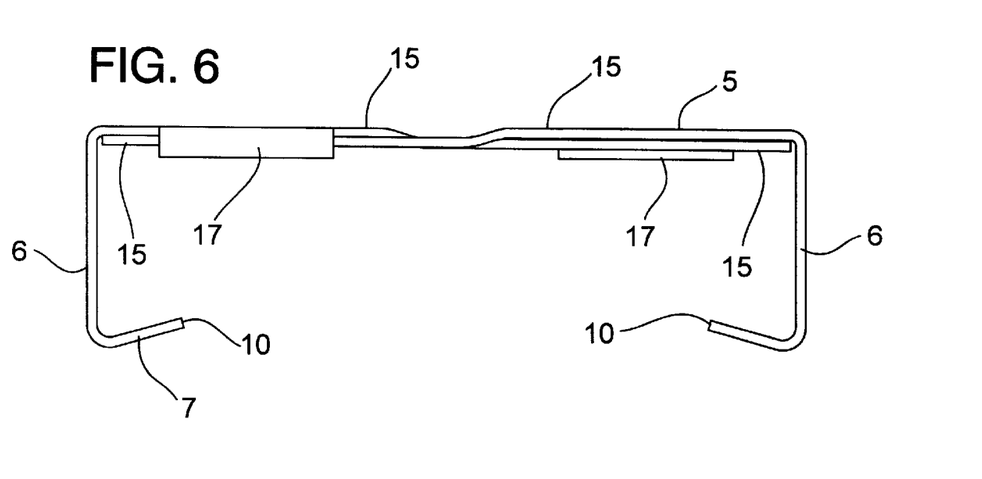
FIG. 6 illustrates joined first and second clamp members in a bottom view elevation.

FIG. 6 illustrates joined first and second clamp members in a bottom view elevation wherein like numerals reference like elements.

Figure 7:
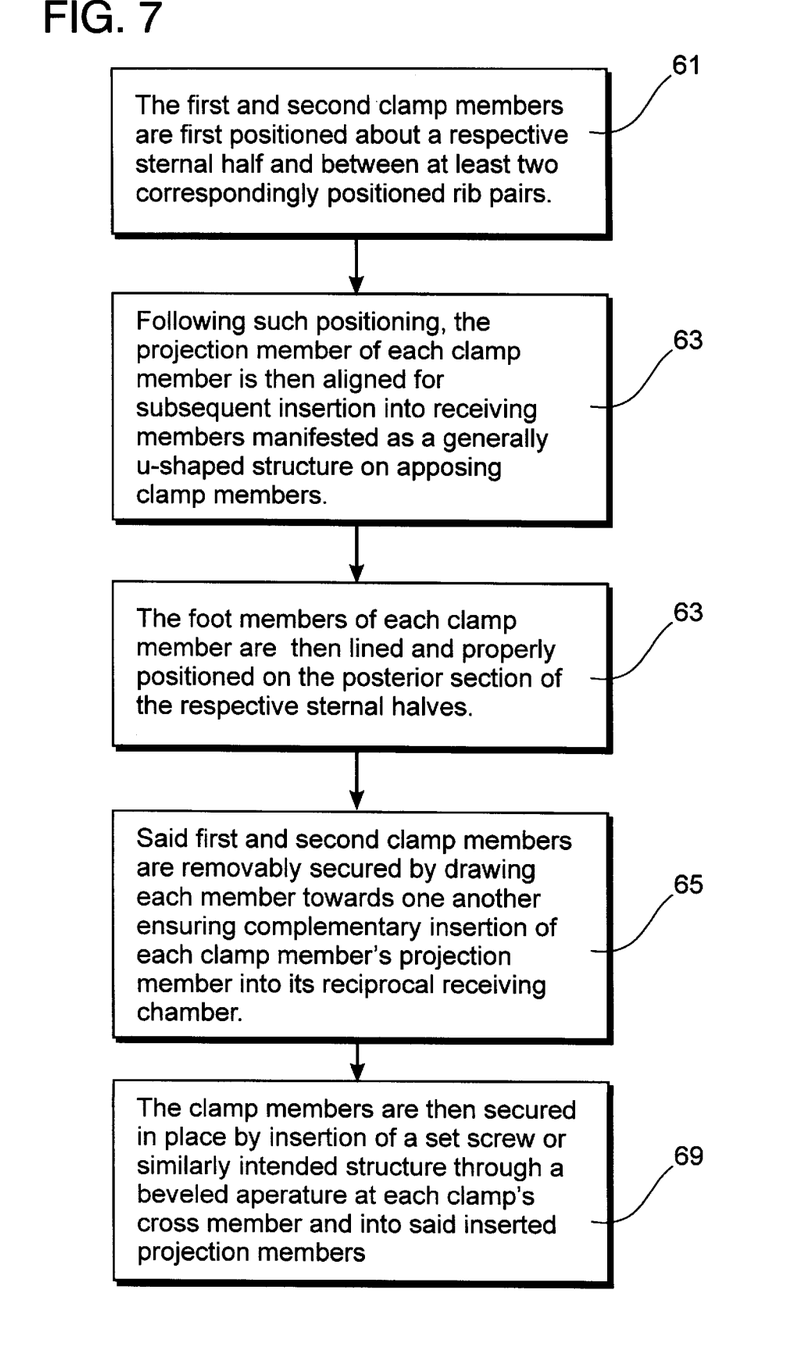
FIG. 7 illustrates a block diagram of method of sequence steps when deploying first and second clamp members of the instant invention to facilitate closure and healing of a severed sternum.

FIG. 7 illustrates a block diagram of the method sequence steps when deploying first and second clamp members of the instant invention to facilitate closure and healing of a several sternum.

In FIG. 7 first and second clamp members are first positioned about a respective sternal half and between at least two correspondingly positioned rib pairs 61. Following such positioning, the projection member of each clamp member is then aligned for subsequent insertion into receiving members manifested as a generally Ushaped structure on apposing clamp members 63. The foot members of each clamp member are then aligned and properly positioned on the posterior section of the respective sternal halves 65 and said first and second clamp members are removably secured by drawing each member towards one another ensuring complementary insertion of each clamp member's projection member into its reciprocal receiving chamber 67. The clamp members are then secured in place by insertion of a set screw or similarly intended structure through a beveled aperture at each clamp's cross member and into said inserted projection members 69.

While this invention has been described to illustrative embodiments, this description is not to be construed in a limiting sense. Various modifications and combinations of the illustrative embodiments as well as other embodiments will be apparent to those skilled in the art upon referencing this disclosure. It is therefore intended that this disclosure encompass any such modifications or embodiments.

What is claimed is:

1. A sternal closure device comprising impermanently joined first and second clamp structures which are adapted for intercostal positioning between at least two correspondingly positioned rib pairs substantially surrounding a patient's sternum each clamp having a cross member a plurality of integrated leg and foot portions, a plurality of sternum engagement surfaces, an end portion, a projection member and a generally Ushaped receiving chamber wherein the end portion of said first clamp member substantially extends toward the end portion of said second clamp member when first and second clamp projection members are slidably received and secured in said first and second clamp receiving chambers.

2. The device of claim 1 wherein said sternum engagement surfaces contacts the frontal portion of a sternum.

3. The device of claim 1 wherein said sternum engagement surfaces contacts the posterior portion of a sternum.

4. The device of claim 1 wherein said sternum engagement surfaces contact the frontal and posterior portion of a sternum.

5. The device of claim 1 wherein said projection members and said receiving chambers further comprise a securing means to facilitate the operative securing of said first and second clamp structures to one another.

6. The surgical device of claim 1 wherein said clamp members are made from biocompatible material.

7. The surgical device of claim 6 wherein said material comprises a radiolucent biocompatible material.

8. The sternal closure device of claim 1 wherein said first and second clamp structures are sized and dimensioned to engage opposite sides of a patient's severed sternum while positioned intercostally between at least two corresponding rib pairs.

9. The sternal closure device of claim 1 further comprising a quick release means for releasing operatively secured first and second clamp structures.

10. A method of closing a patient's sternum following a sternotomy comprising:

(A) placing first and second clamp members about a respective sternal half and between at least two correspondingly positioned rib pairs;

(B) aligning opposed projection members of each clamp member for subsequent insertion into receiving chambers of each clamp;

(C) positioning foot members of each clamp member upon the posterior section of said sternum to maximize sternal healing surface contact; and, (D) removably securing said projection members within said receiving chambers.

* * * * *